United States Patent
Song et al.

(10) Patent No.: US 11,576,639 B2
(45) Date of Patent: Feb. 14, 2023

(54) METHOD, SYSTEM, DEVICE AND MEDIUM FOR DETERMINING A BLOOD FLOW VELOCITY IN A VESSEL

(71) Applicant: BEIJING KEYA MEDICAL TECHNOLOGY CO., LTD., Beijing (CN)

(72) Inventors: Qi Song, Seattle, WA (US); Ying Xuan Zhi, Seattle, WA (US); Yuwei Li, Bellevue, WA (US); Youbing Yin, Kenmore, WA (US); Shubao Liu, College Park, MD (US); Bin Ma, Bellevue, WA (US)

(73) Assignee: BEIJING KEYA MEDICAL TECHNOLOGY CO., LTD., Beijing (CN)

( * ) Notice: Subject to any disclaimer, the term of this patent is extended or adjusted under 35 U.S.C. 154(b) by 686 days.

(21) Appl. No.: 16/576,034

(22) Filed: Sep. 19, 2019

(65) Prior Publication Data

US 2020/0085396 A1    Mar. 19, 2020

Related U.S. Application Data

(60) Provisional application No. 62/733,607, filed on Sep. 19, 2018.

(51) Int. Cl.
| | |
|---|---|
| *A61B 6/00* | (2006.01) |
| *A61B 6/12* | (2006.01) |
| *A61B 5/00* | (2006.01) |
| *A61B 34/10* | (2016.01) |

(52) U.S. Cl.
CPC ............ *A61B 6/507* (2013.01); *A61B 5/7278* (2013.01); *A61B 6/12* (2013.01); *A61B 6/466* (2013.01); *A61B 6/504* (2013.01); *A61B 2034/105* (2016.02)

(58) Field of Classification Search
CPC .................................................. A61B 6/507
See application file for complete search history.

(56) References Cited

PUBLICATIONS

Fischer JJ, Samady H, McPherson JA, et al. "Comparison between visual assessment and quantitative angiography versus fractional flow reserve for native coronary narrowings of moderate severity." Am J Cardiol. 2002;90(3):210-215.
Tu S, Barbato E, Kószegi Z, et al. Fractional flow reserve calculation from 3-dimensional quantitative coronary angiography and TIMI frame count: a fast computer model to quantify the functional significance of moderately obstructed coronary arteries. JACC Cardiovasc Interv. 2014;7(7):768-777.

*Primary Examiner* — Joseph M Santos Rodriguez
(74) *Attorney, Agent, or Firm* — Bayes PLLC (57) ABSTRACT

Method, system, device and medium for determining a blood flow velocity in a vessel are provided. An example method includes receiving a 3D model of the vessel, which is reconstructed based on X-ray angiography images of the vessel. The method further includes specifying a segment of the 3D model by a start landmark and a termination landmark. Moreover, the method includes determining the blood flow velocity based on length of the segment and perfusion time for the segment by normalizing the blood flow velocity to correspond to a cardiac cycle. The method has a better accuracy in calculating blood flow velocity, and requires no additional modalities other than the original X-ray angiogram sequences used to visualize coronary arteries.

20 Claims, 9 Drawing Sheets

METHOD, SYSTEM, DEVICE AND MEDIUM FOR DETERMINING A BLOOD FLOW VELOCITY IN A VESSEL

CROSS-REFERENCE TO RELATED APPLICATION

This application claims the benefit of priority to U.S. Provisional Application No. 62/733,607 filed on Sep. 19, 2018, the entire contents of which are incorporated herein by reference.

TECHNICAL FIELD

The disclosure generally relates to calculation and analysis of blood flow velocity. More specifically, this disclosure relates to a method, a system and a device for determining a blood flow velocity in a vessel.

BACKGROUND

Myocardial ischemia arises due to insufficient blood supply to the heart as a result of coronary artery lesions. Conventional assessment of coronary lesions requires coronary X-ray angiography where X-ray images are captured while a contrast agent is being injected into coronary vessels. X-ray angiography is an economical and convenient measure for visualizing the geometry, occlusion, blood development abnormality of coronary vessels. Yet, visual assessment of stenosis from X-ray angiography does not directly predict the functional blood supply and the hemodynamic significance at a stenosis. As a result, interventional cardiologists tend to overestimate the significance of moderate coronary lesions, which may lead to unnecessary percutaneous coronary intervention. The Fractional Flow Reserve (FFR) is an index acquired by maneuvering a pressure guide wire to gauge the pressure at the distal end of a lesion and the catheter end, thus giving a more precise appraisal of the functional blood flow and subsequently informing the decision of coronary revascularization. However, several limitations of FFR include the cost of wire and occasional adverse response to the wire and other related chemical agents. To circumvent these limitations, virtual FFR, the estimation of FFR without invasive pressure measurements, was introduced by leveraging the recent technological advances in medical imaging and high-performance computing. The existing virtual FFR methods are based on physics models such as computational fluid dynamics solvers or empirical fluid dynamic equations, both of which utilize a coronary blood flow velocity calculation adapted from the Thrombolysis in Myocardial Infarction frame count method. Particularly, blood flow velocity is used as boundary condition in performing computational fluid dynamics solvers or as intermediate parameters in empirical fluid dynamic equations to determine the descriptors and parameters of the physics models, so as to determine FFR. While calculating blood flow velocity, the number of frames needed for contrast agent to reach distal landmarks is counted. By combining frame counts with the 3-D geometry of the coronary vessel of interest, the average blood flow velocity can be derived. Nonetheless, this method does not take into consideration the variation of blood flow velocity at various phases of a cardiac cycle.

Figure 1:
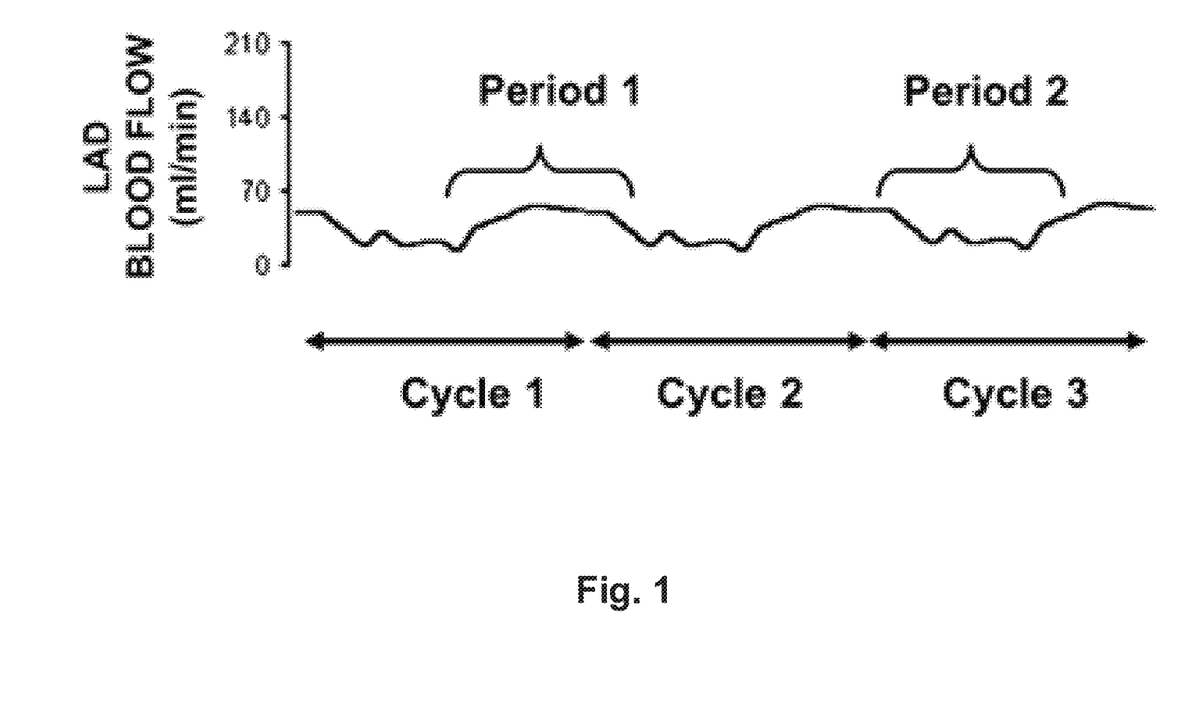
FIG. 1 illustrates blood flow velocity at a left anterior descending artery for three cardiac cycles.

FIG. 1 illustrates blood flow velocity at a left anterior descending artery for three cardiac cycles, from cycle 1 to cycle 3. As seen in FIG. 1, blood flow fluctuates dramatically in one cardiac cycle, and frame count that starts and ends at different phases, for example period 1 and period 2, may indicate significantly different flow velocities for the same vessel segment. And the blood flow velocity calculated for each of period 1 and period 2 cannot accurately deliver the blood flow velocity attribute for a complete cardiac cycle.

Conventional algorithms may include utilizing the electrocardiography (ECG) signal coupled with angiograms to estimate cardiac cycles and normalize frame counts. However, recording ECG and aligning ECG with X-ray sequences entail considerable workload and discourage clinical utilization. Other algorithms, such as optical flow, are widely used in object tracking to analyze the dynamics of coronary arteries solely from X-ray angiograms. Such methods also have drawbacks as being sensitive to noise and table movement.

SUMMARY

The present disclosure is provided to overcome the technical defects in the traditional method for determining blood flow velocity in a vessel. Generally, the present disclosure introduces the normalization of the blood flow velocity with respect to a complete cardiac cycle. In this manner, the influence of cardiac cycles on the blood flow velocity may be taken into account and the normalized blood flow velocity may correspond to a complete cardiac cycle.

In one aspect, the present disclosure provides a method for determining a blood flow velocity in a vessel. The method includes receiving a 3D model of the vessel, which is reconstructed based on X-ray angiography images of the vessel. The method further includes specifying a segment of the 3D model by a start landmark and a termination landmark. Moreover, the method includes determining the blood flow velocity based on length of the segment and perfusion time for the segment by normalizing the blood flow velocity to correspond to a cardiac cycle.

In another aspect, the present disclosure provides a system for determining a blood flow velocity in a vessel. The system includes an interface configured to receive a 3D model of the vessel, which is reconstructed based on X-ray angiography images of the vessel. The image is acquired by an imaging device. The system also includes a processor configured to specify a segment of the 3D model by a start landmark and a termination landmark. The processor is further configured to determine the blood flow velocity based on length of the segment and perfusion time for the segment by normalizing the blood flow velocity to correspond to a cardiac cycle.

In yet another aspect, the present disclosure provides a non-transitory computer readable medium storing instructions. The instructions, when executed by a processor, perform a method for determining a blood flow velocity in a vessel. The method includes receiving a 3D model of the vessel, which is reconstructed based on X-ray angiography images of the vessel. The method also includes specifying a segment of the 3D model by a start landmark and a termination landmark. The method further includes determining the blood flow velocity based on length of the segment and perfusion time for the segment by normalizing the blood flow velocity to correspond to a cardiac cycle.

The method, system, device and medium for determining a blood flow velocity in a vessel have a better accuracy in calculating blood flow velocity, and require no additional modalities other than the original X-ray angiogram sequences used to visualize coronary arteries.

It is to be understood that the foregoing general description and the following detailed description are exemplary and explanatory only, and are not restrictive of the invention as claimed.

BRIEF DESCRIPTION OF THE DRAWINGS

In the drawings, which are not necessarily drawn to scale, like reference numerals may describe similar components in different views. Like reference numerals having letter suffixes or different letter suffixes may represent different instances of similar components. The drawings illustrate generally, by way of example, but not by way of limitation, various embodiments, and together with the description and claims, serve to explain the disclosed embodiments. Such embodiments are demonstrative and not intended to be exhaustive or exclusive embodiments of the present method, device, system, or non-transitory computer readable medium having instructions thereon for implementing the method.

DETAILED DESCRIPTION

Figure 2:
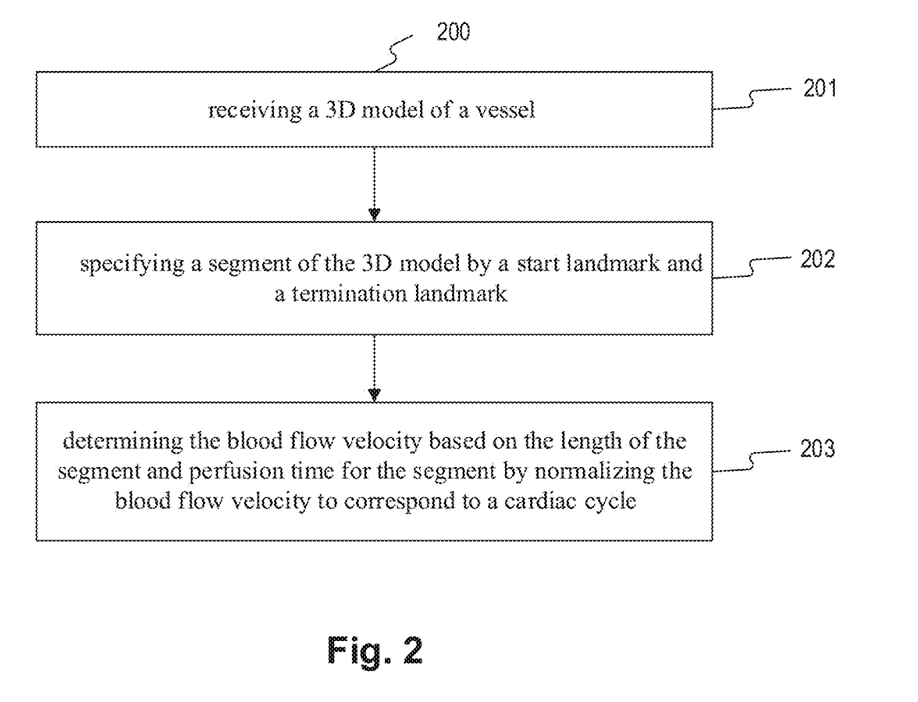
FIG. 2 illustrates a method for determining a blood flow velocity in a vessel according to an embodiment of the present disclosure.

FIG. 2 illustrates a method for determining a blood flow velocity in a vessel according to an embodiment of the present disclosure. As shown in FIG. 2, the blood flow velocity determination process 200 begins with receiving a 3D model of the vessel (step 201). In some embodiments, the 3D model of the vessel may be received from current 3D reconstruction software commercially available. Besides, an additional reconstruction step may be incorporated to obtain the 3D model of the vessel based on the images of the vessel. As an example, the images may be a series of 2D computed tomographic images along the centerline of the vessel. As another example, a 3D model of the vessel may be obtained by reconstruction based on X-ray angiography images of the vessel at two different projection directions. The technical term "receive" means any manner of obtaining, directly or indirectly, with or without additional image processing and modeling (noise reduction, cropping, reconstruction, etc.).

In some embodiments, the vessel may be a coronary artery.

Based on the received 3D model, by labeling a start landmark and a termination landmark, a segment of the 3D model may be specified (step 202). In some embodiments, the start landmark and the termination landmark may be selected and labeled manually or automatically. Based on the specified segment of blood flow, the average velocity of the blood perfusing through such segment may be determined as the blood flow velocity. In some embodiments, during the process of coronary angiography, a catheter may be inserted into the blood vessel and threaded to an entry of coronary arteries. A contrast agent may be injected, then carried through the arteries by blood, during which a series of X-ray images may be captured. The perfusion time that the contrast agent flows through the specified segment, i.e. from the start landmark to the termination landmark, may be longer or less than, or equal to a cardiac cycle.

The blood flow velocity may be determined based on length of the segment and perfusion time. As an example, the average blood flow velocity may be determined based the following formula (1):

$$v = \frac{L}{T}, \quad \text{formula (1)}$$

where v stands for average blood flow velocity, L stands for length of the segment and T is the perfusion time. The normalization of the blood flow velocity with respect to a complete cardiac cycle may be integrated into (with) such determination process for the blood flow velocity (step 203). The method 200 normalizes blood flow velocity with respect to a full cardiac cycle only based on X-ray angiography images of the vessel and its image analysis, without additional modalities for providing phasic information of cardiac cycles. In this manner, the influence of cardiac cycles on the blood flow velocity may be taken into account and the normalized blood flow velocity may correspond to a complete cardiac cycle.

In some embodiments, the length of the segment of the blood flow may be calculated according to the location of the start landmark and the termination landmark on the segment and the 3D model of the vessel.

In some embodiments, to acquire the perfusion time, a first frame where blood perfuses the start landmark and a second frame where blood perfuses the termination landmark may be recorded firstly, and then a frame number difference between the first frame and the second frame may be determined. By dividing the frame number difference by frame rate (e.g., frames per second), the perfusion time may be obtained. Means of obtaining the perfusion time are not limited to this, as the above description is only one of the many available and feasible means.

In some embodiments, during the process of coronary angiography, a catheter may be inserted into the blood vessel and threaded to an entry of coronary arteries. A contrast agent may be injected, then carried through the arteries by blood, during which a series of X-ray images may be captured. As soon as the contrast agent enters the opening of a coronary artery, for example, the left main of left coronary arteries, a landmark may be manually or automatically selected. In some embodiments, the cardiac cycle may be estimated manually or automatically. Particularly, by tracking a motion of a track landmark remaining immobile relative to the aorta, the periodic motion of the aorta may be tracked since the track landmark may serve as a surrogate of the aorta. In some embodiments, the tip of the catheter for coronary angiography resides immobile relative to the aorta, and thus may be used as the track landmark. It is easier to visualize and locate the tip of the catheter compared to other track landmarks.

Figure 3:
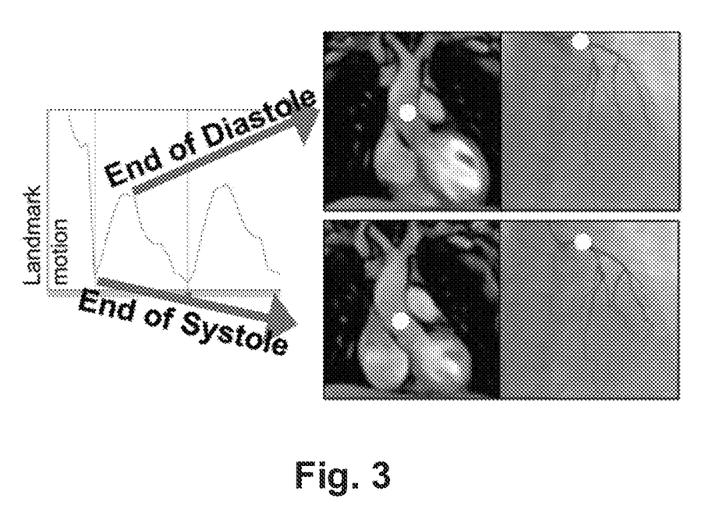
FIG. 3 illustrates the motion of tracking landmark and images of the coronary arteries at diastole and systole end points according to an embodiment of the present disclosure.

Further, the periodic motion of the aorta reflects accurately the attribute of the cardiac cycle. FIG. 3 illustrates the motion of tracking landmark and images of the coronary arteries at diastole and systole end points according to an embodiment of the present disclosure. Specifically, at the end of ventricular diastole, the aorta ascends in relation to the thoracic cavity, resulting in a higher position of the start landmark in the field of view as shown in the upper parts of FIG. 3, while at the end of ventricular systole, the aorta descends in relation to the thoracic cavity, resulting in a lower position of the landmark in the field of view, as shown in the upper parts of FIG. 3. In such embodiments, the troughs may be identified from the track landmark motion profile as the systole end points, and consequently the average intervals between each pair of the adjacent systole end points may be determined to obtain the period of the cardiac cycle. In some embodiments, the interval between all adjacent systole end points may be averaged to compute the heart beats per minute and/or the number of frames per cycle. The performance of such automatic tracking algorithm may be validated with respect to manual determination of cardiac cycles from X-ray sequences, as shown in FIG. 4.

Figure 4:
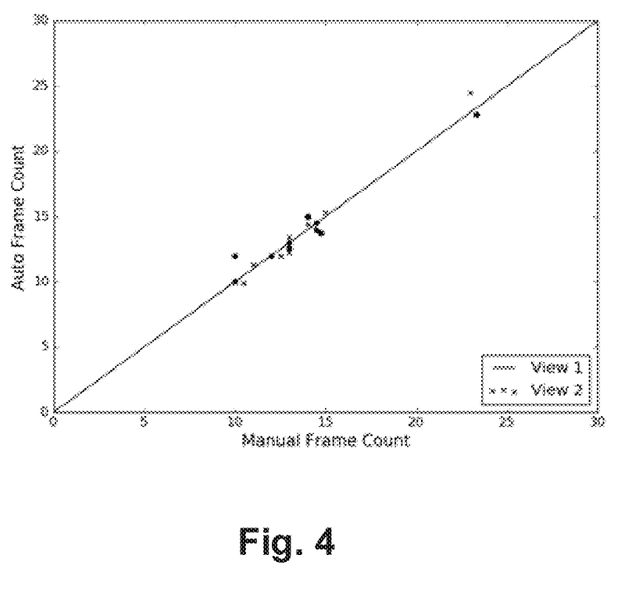
FIG. 4 illustrates comparison results of manual frame counts and automatically calculated frame counts for one cardiac cycle according to an embodiment of the present disclosure.

FIG. 4 illustrates comparison results of manually and automatically counting the frames according to an embodiment of the present disclosure. As can be seen in FIG. 4, in two different views of the same X-ray sequences, the automatically calculated frame counts for one cardiac cycle comply substantially with the manual frame counts for the one cardiac cycle.

Figure 5:
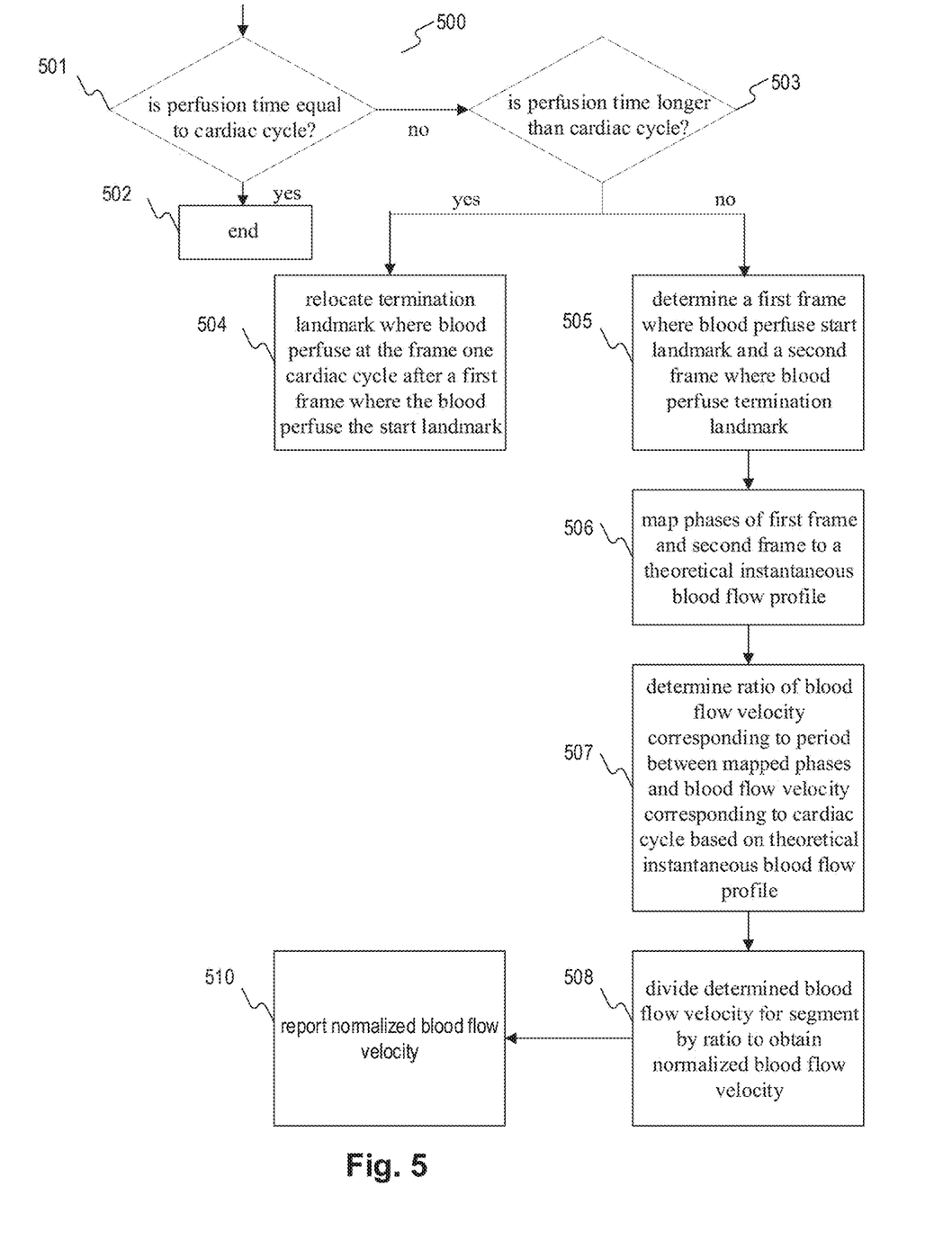
FIG. 5 illustrates a process of normalizing blood flow velocity to correspond to a cardiac cycle according to an embodiment of the present disclosure.

In some embodiments, normalizing the blood flow velocity to correspond to a cardiac cycle may include several cases, depending on the relationship between perfusion time and the cardiac cycle. FIG. 5 illustrates process of normalizing blood flow velocity to correspond to a cardiac cycle according to an embodiment of the present disclosure. Process 500 starts from step 501, determining whether the perfusion time is equal to the cardiac cycle. If the perfusion time is equal to the cardiac cycle, the process ends at step 502, which means the time that blood flow through the specified segment exactly equals the cardiac cycle, the perfusion time may be directly used for determining blood flow velocity. If the perfusion time is not equal to the cardiac cycle, then in step 503, the process can include further determining whether perfusion time is longer than cardiac cycle. If the perfusion time is longer than the cardiac cycle, then the termination landmark may be relocated to another frame which is exactly one cardiac cycle after the first frame where the blood perfuses the start landmark, as in step 504.

Figure 6:
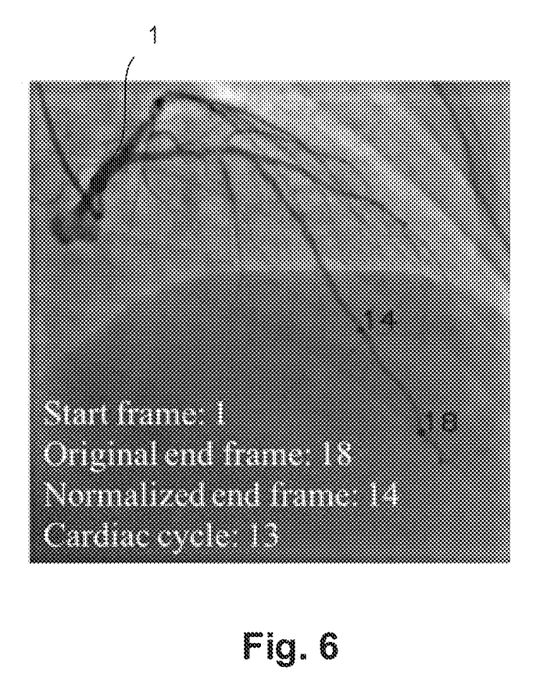
FIG. 6 illustrates an example of normalizing blood flow velocity to correspond to a cardiac cycle when the perfusion time is longer than the cardiac cycle according to an embodiment of the present disclosure.

FIG. 6 illustrates an example of normalizing blood flow velocity to correspond to a cardiac cycle when the perfusion time is longer than the cardiac cycle according to an embodiment of the present disclosure in step 504. As can be seen in FIG. 6, the start frame (e.g., frame 1) represents the starting frame where blood perfuses the start landmark, and the original end frame (e.g., frame 18) represents the end frame where blood perfuses the termination landmark. In order to conform to a cardiac cycle of 13 frames, the termination landmark in original end frame (e.g., frame 18) may be relocated to another frame (e.g., frame 14), which is exactly one cardiac cycle, i.e. 13 frames, after the first frame (frame 1). In this example, frame 14 becomes the normalized end frame, and the termination landmark is now located at this normalized end frame.

Back to FIG. 5, in step 503, determining whether perfusion time is longer than cardiac cycle, if the perfusion time is less (shorter) than the cardiac cycle, then in step 505, a first frame and a second frame may be obtained, and the first frame and the second frame may be mapped into a theoretical instantaneous blood flow profile which describes the blood flow states in theory, as in step 506. In some embodiments, the theoretical instantaneous blood flow profile mentioned in Fischer J J, Samady H, McPherson J A, et al. "Comparison between visual assessment and quantitative angiography versus fractional flow reserve for native coronary narrowings of moderate severity." AM J Cardiol. 2002; 90(3):210-215 may be adopted herein. Besides, the theoretical instantaneous blood flow profile mentioned may also be derived from considerable exampling data based on clinical measurements of blood flow velocity.

In step 510, the process can include reporting the normalized blood flow velocity. The normalized blood flow velocity can be reported digitally, audibly, and/or visually by a system implementing the process.

Figure 7:
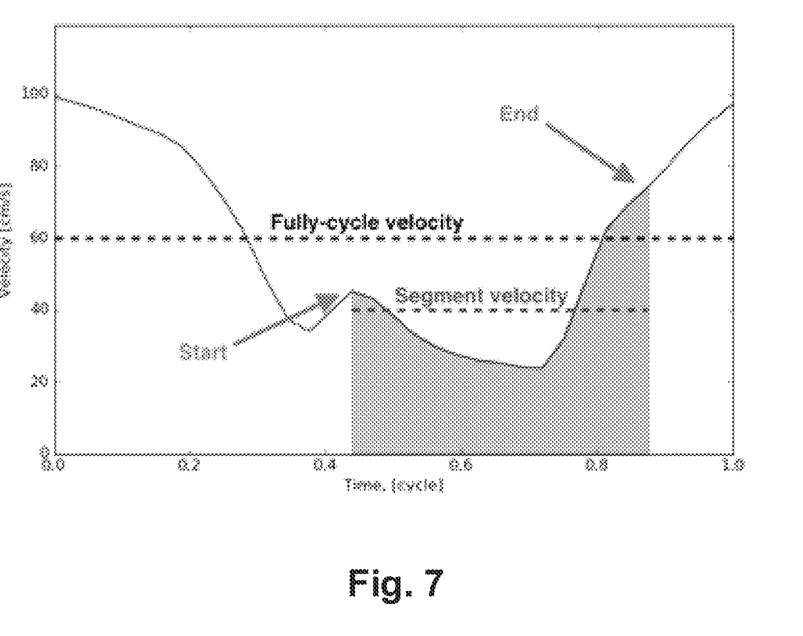
FIG. 7 illustrates an example of normalizing blood flow velocity to correspond to a cardiac cycle in the case of perfusion time shorter than the cardiac cycle according to an embodiment of the present disclosure.

FIG. 7 illustrates an example of normalizing blood flow velocity to correspond to a cardiac cycle in the case of perfusion time less than the cardiac cycle according to an embodiment of present disclosure. As can been seen in FIG. 7, the curve describes a theoretical blood flow velocity distribution and based on such curve, a theoretical full-cycle velocity may be obtained, and according to the mapped phases of the first frame, i.e. the start phase, and the mapped phases of the first frame, i.e. the end phase, a theoretical segment velocity may be also obtained. Further in step 507, determining the ratio of the blood flow velocity corresponding to the period between the mapped phases and the blood flow velocity corresponding to the cardiac cycle based on the theoretical instantaneous blood flow profile, i.e. the ratio between theoretical segment velocity between the mapped phases and theoretical full-cycle velocity. The inventor found that such ratio is generally consistent with the ratio of the actual determined blood flow velocity (between the corresponding start phase and end phase) and the actual blood flow velocity for a full cardiac cycle. Since the ratio and the actual determined blood flow velocity for the segment are obtained, the actual normalized blood flow velocity may be easily determined by dividing actual determined blood flow velocity for the segment by the ratio, as in step 508. Such normalization process may recover and reproduce the blood flow velocity for a full cycle based on the actual determined blood flow velocity, which may correspond to a part of the full cycle. The part may be located anywhere within the full cycle, and such normalization process may be useful especially when the interval between the start phase and end phase is relatively narrow with respect to the full cardiac cycle.

Figure 8:
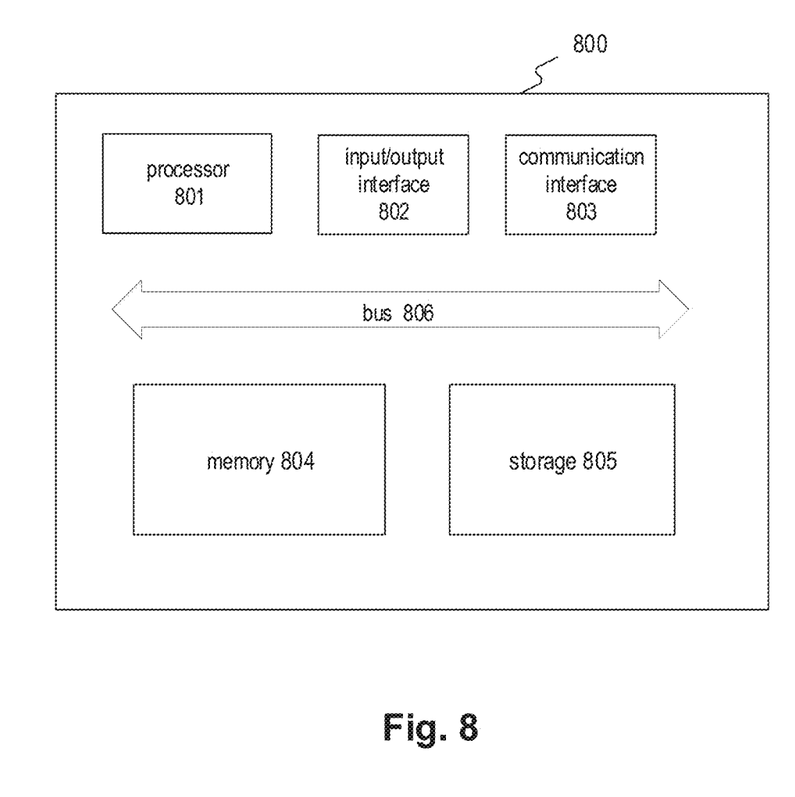
FIG. 8 illustrates a system for determining a blood flow velocity in a vessel according to an embodiment of the present disclosure.

FIG. 8 illustrates a system for determining a blood flow velocity in a vessel according to an embodiment of present disclosure. The system 800 may include a processor 801 and a communication interface 803. The communication interface 803 may be configured to receive a 3D model of the vessel, which is reconstructed based on X-ray angiography images of the vessel, or receive X-ray angiography images of the vessel. The processor 801 may be configured to specify a segment of the 3D model by a start landmark and a termination landmark, and determine the blood flow velocity based on length of the segment and perfusion time for the segment by normalizing the blood flow velocity to correspond to a cardiac cycle. Additionally, system 800 may further include an input/output interface 802, a memory 804, and a storage 805. Respective components of system 800 are mutually connected via, for example, a bus 807. The system 800 realizes at least functions or methods described in the embodiment through cooperation of the processor 801, the memory 804, the storage 806, the input/output interface 802 and the communication interface 803.

The processor 801 executes at least functions or methods that are realized by code or instructions included in a program stored in the storage 805. Examples of the processor 801 include a central processing unit (CPU), a micro processing unit (MPU), a graphics processing unit (GPU), a microprocessor, a processor core, a multiprocessor, an application-specific integrated circuit (ASIC), and a field programmable gate array (FPGA).

The memory 804 temporarily stores the program loaded from the storage 805 and provides a work area to the processor 801. Various pieces of data generated while the processor 801 is executing the program are also temporarily stored in the memory 804. The memory 804 includes, for example, a random access memory (RAM) and a read only memory (ROM).

The storage 805 stores, for example, the program that is executed by the processor 801. The storage 805 includes, for example, a hard disk drive (HDD), a solid state drive (SSD), and a flash memory.

The input/output interface 802 includes an input device that inputs various manipulations to the system 800, and an output device that outputs a processing result of the system 800. For example, input/output interface 802 may provide a digital, audible, and/or visual report of a blood flow velocity determined by system 800. Thus, input/output interface 802 may include a user interface such as a graphical user interface (GUI) and/or one or more speakers.

The communication interface 803 performs transmission and reception of various pieces of data via network. The communication may be executed by a cable or wirelessly, and any communication protocol may be used as long as communication with each other is possible. The communication interface 803 has a function of executing communication to and from the system 800 and transmits various pieces of data. The communication interface 803 can, for example, provide a digital output from input/output interface 802 to an external system (not shown). The digital output may be configured to serve as an input or control signal for the external system. The external system may include, for example, a device for medical intervention, such as an angioplasty device.

The program for operating the system 800 according to the embodiment may be provided in a state in which the program is stored in a computer-readable storage medium. The storage medium can store the program in a "non-transitory tangible medium". Further, the program includes, for example, a software program or a computer program.

Furthermore, at least some of processes in system 800 may be realized by cloud computing configured of one or more computers. In addition, at least some of processes in system 800 can be performed by an alternative device. Furthermore, at least some of processes of each functional unit realized by the processor 801 can be performed by an alternative device.

Figure 9:
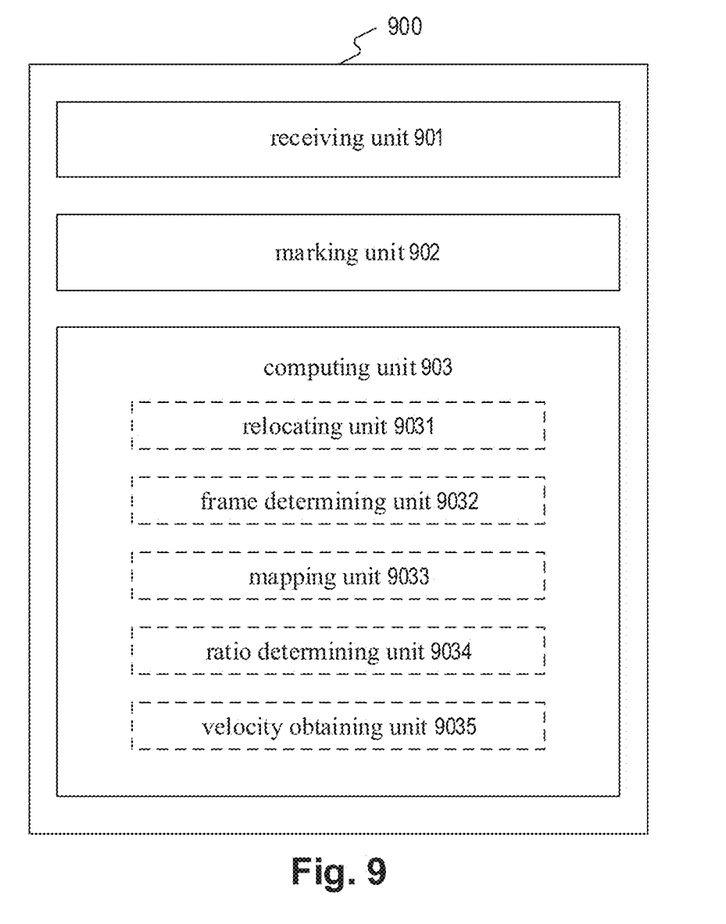
FIG. 9 illustrates a device for determining a blood flow velocity in a vessel according to an embodiment of the present disclosure.

FIG. 9 illustrates a device for determining a blood flow velocity in a vessel according to an embodiment of present disclosure. As shown in FIG. 9, the device 900 may include a receiving unit 901, a marking unit 902, and a determining unit 903. The receiving unit 901 may be configured to receive a 3D model of the vessel; the 3D model is constructed based on X-ray angiography images of the vessel. The specifying unit 902 may be configured to specify a segment of the 3D model by a start landmark and a termination landmark. The determining unit 903 may be configured to determine the blood flow velocity based on length of the segment and perfusion time for the segment by normalizing the blood flow velocity to correspond to a cardiac cycle.

In some embodiments, the determining unit 903 may further comprise a relocating unit 9041, a frame determining unit 9042, a mapping unit 9043, a ratio determining unit 9044 and a velocity obtaining unit 9045. In some embodiments that the perfusion time is longer than the cardiac cycle, to normalize the blood flow velocity to correspond to a cardiac cycle the relocating unit 9031 may be configured to relocate the termination landmark where blood perfuses to a new frame one cardiac cycle after a first frame where the blood perfuses the start landmark. In some other embodiments that the perfusion time is less than the cardiac cycle, to normalize the blood flow velocity to correspond to a cardiac cycle, the frame determining unit 9032 may be configured to determine a first frame where blood perfuses the start landmark and a second frame where blood perfuses the termination landmark; the mapping unit 9033 may be configured to map the phases of the first frame and the second frame to a theoretical instantaneous blood flow profile; the ratio determining unit 9034 may be configured to determine the ratio of the blood flow velocity corresponding to the period between the mapped phases and the blood flow velocity corresponding to the cardiac cycle based on the theoretical instantaneous blood flow profile; and the velocity obtaining unit 9035 may be configured to divide the determined blood flow velocity for the segment by the ratio to obtain the normalized blood flow velocity. Here, at least the marking unit 902 and the computing unit 903 (optionally, as well as the relocating unit 9031, the frame determining unit 9032, the mapping unit 9033, the ratio determining unit 9034, and the velocity obtaining unit 9035) may be implemented as soft modules and stored in the storage 805 as shown in FIG. 8.

Moreover, while illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application. Further, the steps of the disclosed methods can be modified in any manner, including by reordering steps or inserting or deleting steps. It is intended, therefore, that the descriptions be considered as examples only, with a true scope being indicated by the following claims and their full scope of equivalents.

The above description is intended to be illustrative, and not restrictive. For example, the above-described examples (or one or more aspects thereof) may be used in combination with each other. Other embodiments can be used, such as by one of ordinary skill in the art upon reviewing the above description. Also, in the above Detailed Description, various features may be grouped together to streamline the disclosure. This should not be interpreted as intending that an unclaimed disclosed feature is essential to any claim. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A method for determining a blood flow velocity in a vessel, comprising:
receiving, at an interface of a device, a 3D model of the vessel, the 3D model reconstructed based on X-ray angiography images of the vessel;
specifying, by a processor of the device, a segment of the 3D model by a start landmark and a termination landmark; and
determining, by the processor, the blood flow velocity based on length of the segment and perfusion time for the segment by normalizing the blood flow velocity to correspond to a cardiac cycle,
wherein a device for medical intervention is controlled based on the determined blood flow velocity.

2. The method of claim 1, wherein when the perfusion time is longer than the cardiac cycle, normalizing the blood flow velocity to correspond to a cardiac cycle comprises:
relocating the termination landmark where blood perfuses to a new frame one cardiac cycle after a first frame where the blood perfuses the start landmark.

3. The method of claim 1, wherein when the perfusion time is shorter than the cardiac cycle, normalizing the blood flow velocity to correspond to a cardiac cycle comprises:
determining a first frame where blood perfuses the start landmark and a second frame where blood perfuses the termination landmark;
mapping the phases of the first frame and the second frame to a theoretical instantaneous blood flow profile;
determining the ratio of the blood flow velocity corresponding to the period between the mapped phases and the blood flow velocity corresponding to the cardiac cycle based on the theoretical instantaneous blood flow profile; and
dividing the determined blood flow velocity for the segment by the ratio to obtain the normalized blood flow velocity.

4. The method of claim 1, wherein the vessel comprises a coronary artery.

5. The method of claim 1, further comprising calculating the perfusion time by:
determining a first frame where blood perfuses the start landmark and a second frame where blood perfuses the termination landmark;
determining a frame number difference between the first and second frames; and
dividing the frame number difference by a frame rate to obtain the perfusion time.

6. The method of claim 1, further comprising:
estimating the cardiac cycle automatically.

7. The method of claim 6, wherein estimating the cardiac cycle automatically comprises:
tracking a motion of a track landmark remaining immobile relative to an aorta;
identifying the systole end points from the motion of the track landmark; and
averaging the intervals between each pair of adjacent systole end points to obtain the cardiac cycle.

8. The method of claim 7, wherein the track landmark is located at a tip of a catheter for coronary angiography.

9. A system for determining a blood flow velocity in a vessel, comprising:
an interface configured to receive a 3D model of the vessel, the 3D model reconstructed based on X-ray angiography images of the vessel;
a processor configured to:
specify a segment of the 3D model by a start landmark and a termination landmark; and
determine the blood flow velocity based on length of the segment and perfusion time for the segment by normalizing the blood flow velocity to correspond to a cardiac cycle,
wherein a device for medical intervention is controlled based on the determined blood flow velocity.

10. The system of claim 9, wherein when the perfusion time is longer than the cardiac cycle, the processor is further configured to, when normalizing the blood flow velocity to correspond to a cardiac cycle:
relocate the termination landmark where blood perfuses to a new frame one cardiac cycle after a first frame where the blood perfuses the start landmark.

11. The system of claim 9, wherein when the perfusion time is less than the cardiac cycle, the processor is further configured to, when normalizing the blood flow velocity to correspond to a cardiac cycle:
determine a first frame where blood perfuses the start landmark and a second frame where blood perfuses the termination landmark;
map the phases of the first frame and the second frame to a theoretical instantaneous blood flow profile;
determine the ratio of the blood flow velocity corresponding to the period between the mapped phases and the blood flow velocity corresponding to the cardiac cycle based on the theoretical instantaneous blood flow profile; and
divide the determined blood flow velocity for the segment by the ratio to obtain the normalized blood flow velocity.

12. The system of claim 9, wherein the processor is further configured to estimate the cardiac cycle automatically.

13. The system of claim 12, wherein the processor is configured to, when estimating the cardiac cycle automatically:
track a motion of a track landmark remaining immobile relative to an aorta;
identify the systole end points from the motion of the track landmark; and
average the intervals between each pair of adjacent systole end points to obtain the cardiac cycle.

14. The system of claim 13, wherein the track landmark is located at a tip of a catheter for coronary angiography.

15. A non-transitory computer readable medium storing instructions that, when executed by a processor, perform a method, the method comprising:
receiving a 3D model of the vessel, the 3D model reconstructed based on X-ray angiography images of the vessel;
specifying, by a processor, a segment of the 3D model by a start landmark and a termination landmark; and
determining, by the processor, the blood flow velocity based on length of the segment and perfusion time for the segment by normalizing the blood flow velocity to correspond to a cardiac cycle,
wherein a device for medical intervention is controlled based on the determined blood flow velocity.

16. The non-transitory computer readable medium of claim 15, wherein when the perfusion time is longer than the cardiac cycle, normalizing the blood flow velocity to correspond to a cardiac cycle comprises:
relocating the termination landmark where blood perfuses to a new frame one cardiac cycle after a first frame where the blood perfuses the start landmark.

17. The non-transitory computer readable medium of claim 15, wherein when the perfusion time is less than the cardiac cycle, normalizing the blood flow velocity to correspond to a cardiac cycle comprises:
determining a first frame where blood perfuses the start landmark and a second frame where blood perfuses the termination landmark;
mapping the phases of the first frame and the second frame to a theoretical instantaneous blood flow profile;
determining the ratio of the blood flow velocity corresponding to the period between the mapped phases and the blood flow velocity corresponding to the cardiac cycle based on the theoretical instantaneous blood flow profile; and
dividing the determined blood flow velocity for the segment by the ratio to obtain the normalized blood flow velocity.

18. The non-transitory computer readable medium of claim 15, the method further comprising calculating the perfusion time by:
determining a first frame where blood perfuses the start landmark and a second frame where blood perfuses the termination landmark;
determining a frame number difference between the first and second frames; and
dividing the frame number difference by a frame rate to obtain the perfusion time.

19. The non-transitory computer readable medium of claim 15, the method further comprising:
estimating the cardiac cycle automatically.

20. The non-transitory computer readable medium of claim 19, wherein estimating the cardiac cycle automatically comprises:
tracking a motion of a track landmark remaining immobile relative to an aorta;
identifying the systole end points from the motion of the track landmark; and
averaging the intervals between each pair of adjacent systole end points to obtain the cardiac cycle.

* * * * *